United States Patent [19]
Matsunaga et al.

[11] Patent Number: 5,898,083
[45] Date of Patent: Apr. 27, 1999

[54] SODIUM STYRENESULFONATE HEMIHYDRATE, COMPOSITION THEREOF, AND PROCESS FOR PRODUCTION THEREOF

[75] Inventors: Takahiro Matsunaga, Shinnanyo; Hiroyuki Wakamatsu, Tokuyama, both of Japan

[73] Assignee: Tosoh Corporation, Japan

[21] Appl. No.: 08/969,448

[22] Filed: Nov. 13, 1997

[30]  Foreign Application Priority Data

Nov. 21, 1996  [JP]  Japan .................................. 8-311024

[51] Int. Cl.⁶ ................................................ C07C 303/08
[52] U.S. Cl. .............................................................. 562/87
[58] Field of Search ................................................. 562/87

[56]  References Cited

U.S. PATENT DOCUMENTS

| | | | |
|---|---|---|---|
| 2,822,385 | 2/1958 | Estes | 562/87 |
| 3,079,430 | 2/1963 | Goodshaw et al. | 562/87 |
| 3,382,277 | 5/1968 | Pick | 562/87 |
| 4,110,366 | 8/1978 | Tamabayashi et al. | 562/87 |

FOREIGN PATENT DOCUMENTS

| | | |
|---|---|---|
| 355031059 | 3/1980 | Japan . |
| 6511768 | 1/1968 | Netherlands . |

*Primary Examiner*—Samuel Barts
*Assistant Examiner*—Rosalynd Keys
*Attorney, Agent, or Firm*—Nixon & Vanderhye

[57]  ABSTRACT

A sodium styrenesulfonate hemihydrate is provided. This novel sodium styrenesulfonate hemihydrate solves the problems involved in conventional sodium styrenesulfonate such as decrease of effective component by polymerization during storage and transportation, and drop of commercial value by lumping. A composition containing the sodium styrenesulfonate hemihydrate, and a process for producing the sodium styrenesulfonate hemihydrate and the composition are also provided.

13 Claims, 2 Drawing Sheets

SODIUM STYRENESULFONATE HEMIHYDRATE, COMPOSITION THEREOF, AND PROCESS FOR PRODUCTION THEREOF

BACKGROUND OF THE INVENTION

1. Field of the Invention

The present invention relates to sodium styrenesulfonate hemihydrate, a composition containing the sodium styrenesulfonate hemihydrate, and processes for production thereof.

More specifically, the present invention relates to sodium styrenesulfonate hemihydrate which is a novel styrenesulfonate compound having excellent stability with less polymerization liability, and less lumping liability, a composition containing it, and a process for production thereof.

2. Description of the Related Art

Sodium styrenesulfonate is well known to be produced from an aqueous β-haloethylbenzenesulfonate solution by reaction with an aqueous sodium hydroxide solution.

For example, JP-B-53-23292 discloses a method in which an aqueous β-haloethylbenzenesulfonic acid solution is added dropwise to an alcoholic solution of sodium hydroxide to allow the reaction to proceed at 50–70° C.; JP-A-52-23038 discloses a method in which an aqueous β-haloethylbenzenesulfonic acid solution is added dropwise to 35 wt % sodium hydroxide solution in a nitrogen atmosphere at a temperature of 95–105° C. to allow the reaction proceed to cause crystallization of the product; and J-PB-38-20570 discloses a two-step reaction method in which an aqueous β-haloethylbenzenesulfonic acid solution is added to an aqueous sodium hydroxide solution at room temperature or a lower temperature to produce once sodium salt of β-haloethylbenzenesulfonic acid, then the solution is heated to 80–100° C., and an aqueous sodium hydroxide solution is added thereto to obtain sodium styrenesulfonate in a crystal state.

Sodium styrenesulfonate produced by the above methods is used practically as a dyeing assistant, a surfactant, a viscosity-reducing agent, and so forth.

The sodium styrenesulfonate produced by any of the above conventional methods, however, is less stable in storage and transportation, and can polymerize in a degree of 10% or more by weight in several months to cause decrease of the effective component content, or can cause lumping by bridging between the particles, disadvantageously.

As a countermeasure against the polymerization, a polymerization inhibitor, such as a nitrite salt, hydroquinone, and hydroquinone monomethyl ether, is added after the synthesis and/or solid-liquid separation of the sodium styrenesulfonate, whereby the polymerization is retarded remarkably, and the product is produced and marketed commercially. However, the polymerization inhibition is not sufficient yet, and the large amount of the added polymerization inhibitor poses another problem of drop of the reactivity of the sodium styrenesulfonate. As the countermeasure against the lumping, the conditions of storage and transportation are carefully controlled without a special measure. In some cases, granulation is tried. However, the above countermeasures are not substantially effective.

SUMMARY OF THE INVENTION

The present invention intends to provide sodium styrenesulfonate which does not cause problems of decrease in the effective component content by polymerization during storage and transportation and of loss of the commercial value by lumping.

The present invention intends also to provide a composition containing the above sodium styrenesulfonate.

The present invention intends further to provide processes for producing the above sodium styrenesulfonate.

The sodium styrenesulfonate of the present invention is sodium styrenesulfonate hemihydrate.

The sodium styrenesulfonate composition of the present invention contains the sodium styrenesulfonate hemihydrate at a content of not lower than 50% by weight.

The process for producing the sodium styrenesulfonate hemihydrate or the composition thereof of the present invention comprises reacting an aqueous solution of β-haloethylbenzenesulfonic acid and/or a sodium salt thereof with an aqueous solution of sodium hydroxide at a temperature of not lower than 60° C. to deposit sodium styrenesulfonate anhydrous, collecting the deposit by solid-liquid separation in a state of a wet cake, fluidizing forcedly the wet cake.

In another process of the present invention, the above separated wet cake is exposed to an atmosphere at a temperature of not higher than 60° C. at a relative humidity of not lower than 50%.

In still another process of the present invention, the above separated wet cake is washed with an aqueous sodium hydroxide solution of a concentration of not higher than 5% by weight.

In a further process of the present invention, the reaction slurry before the solid-liquid separation is subjected to adjustment of the concentration of the sodium hydroxide to be in the range of 0.1% to 3% by weight.

DETAILED DESCRIPTION OF THE PREFERRED EMBODIMENT

Investigations were made by the inventors of the present invention as below to solve the above problems.

Figure 1A:
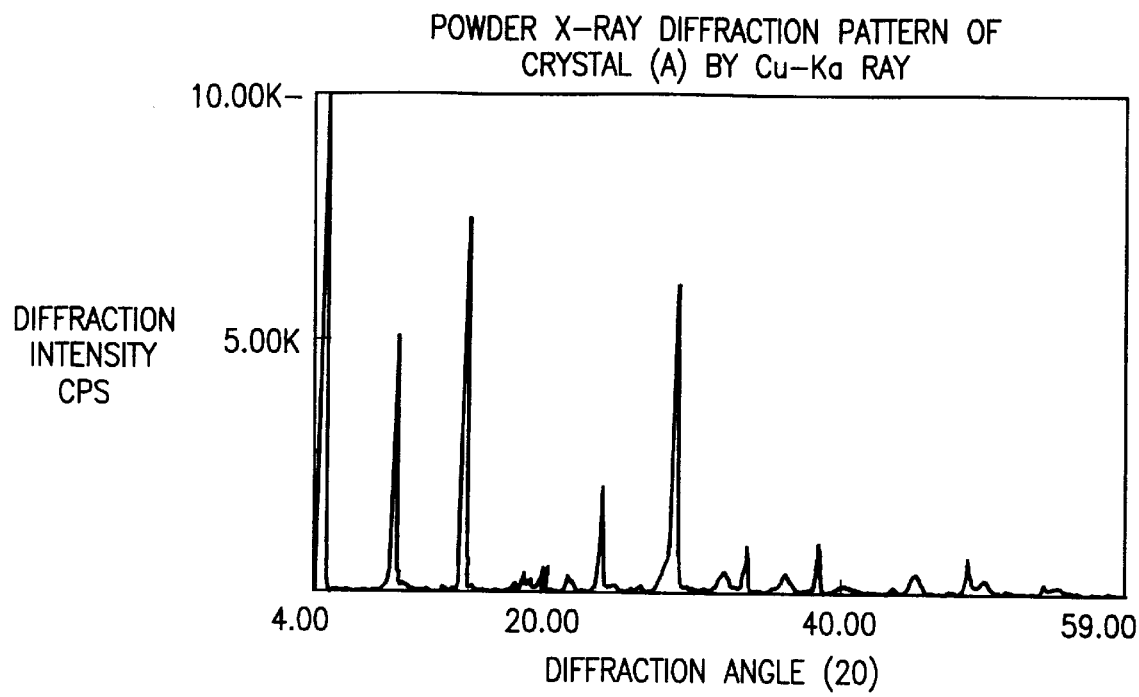
FIG. 1A is a powder X-ray diffraction pattern of sodium styrenesulfonate anhydrous by Cu—Kα ray.
Figure 2A:
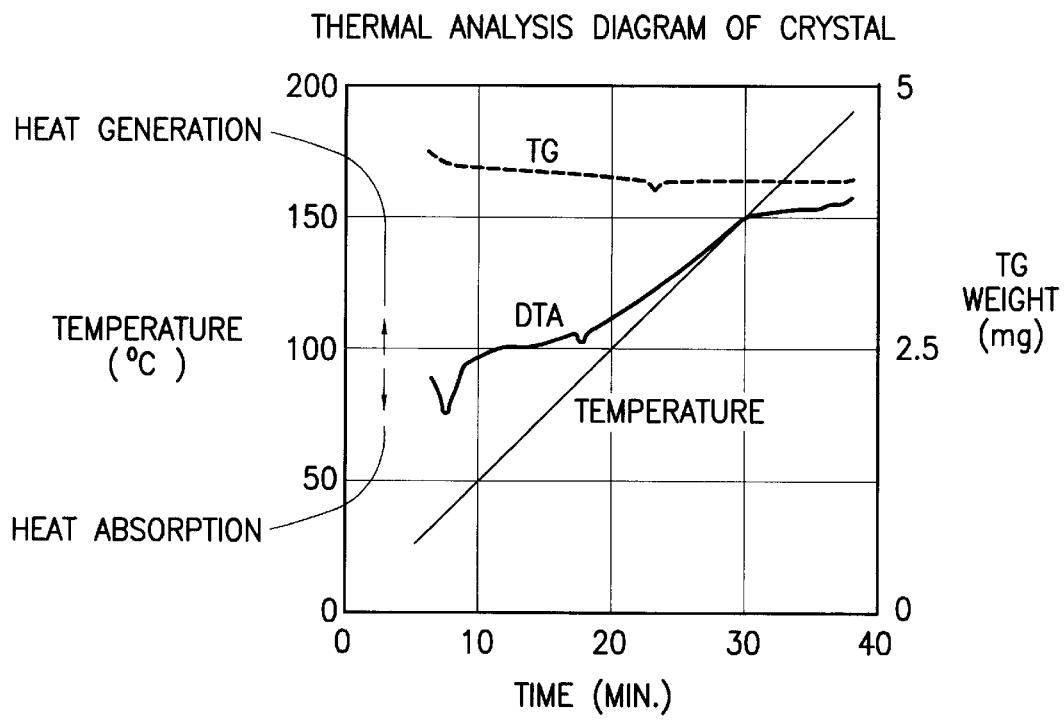
FIG. 2A is a thermal analysis diagram of sodium styrenesulfonate anhydrous.

Firstly, sodium styrenesulfonate was prepared in conventional methods, and the products were examined by chemical analysis, powder X-ray diffractometry, and thermal analysis. Thereby, any of the crystalline sodium styrenesulfonate products by conventional processes was found to be anhydrous. FIG. 1A and FIG. 2A show the analysis results.

Next, the conventional production methods were modified in various manners, and the obtained crystalline sodium styrenesulfonate products were treated in various ways. Consequently, an interesting phenomenon was found such that a wet cake of the sodium styrenesulfonate anhydrous increases its fluidity gradually during blending by means of a single-screw type blender to become dry powder. The powder having been stirred and blended was subjected to structural analysis, and the results below were obtained:

(1) The chemical analysis, the powder X-ray analysis with Cu—Kα ray, and the thermal analysis of the powder showed that the powder had a structure of sodium styrenesulfonate hemihydrate which is completely different from that of the known sodium styrenesulfonate anhydrous. The powder X-ray diffraction pattern thereof was the same as FIG. 1B, and was completely different from that of FIG. 1A.

(2) The sodium styrenesulfonate hemihydrate had also properties different from the known anhydrous. It polymerized little during storage or transportation, and could be handled stably without addition of a large amount of a polymerization inhibitor. Furthermore, no bridging was observed between the particles without causing lump formation during storage for 6 months or longer.

Further, comprehensive investigations were made by the inventors of the present invention to develop industrial technique for producing the above novel sodium styrenesulfonate hemihydrate. Thereby, the present invention has been accomplished.

The present invention relates to a hemihydrate of sodium styrenesulfonate, a composition containing the sodium styrenesulfonate hemihydrate at a content of not lower than 50% by weight, and processes for the hemihydrate and the composition.

The present invention is described below in more detail.

Figure 1B:
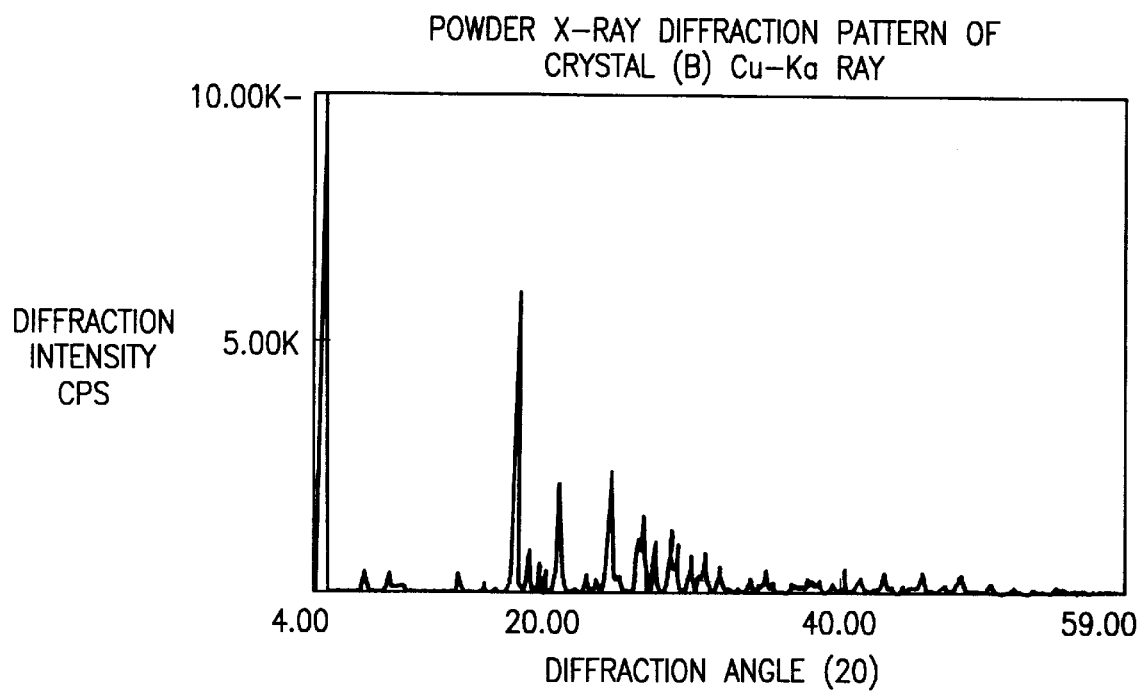
FIG. 1B is a powder X-ray diffraction pattern of sodium styrenesulfonate hemihydrate by Cu—Kα ray.
Figure 2B:
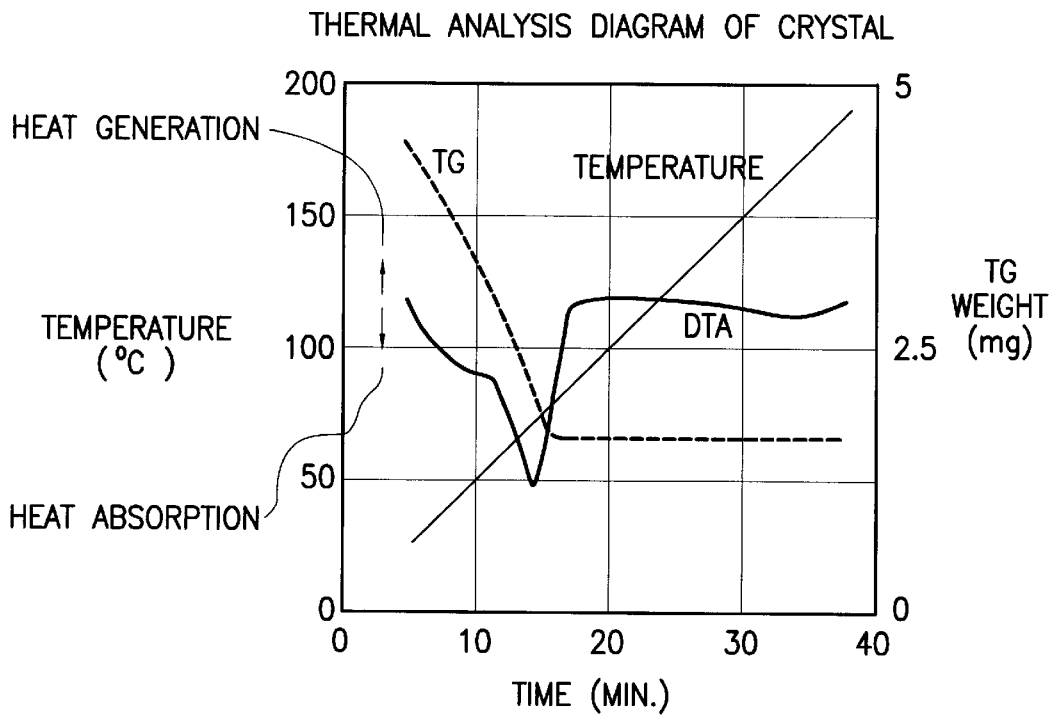
FIG. 2B is a thermal analysis diagram of sodium styrenesulfonate hemihydrate.

The sodium styrenesulfonate hemihydrate of the present invention is a crystalline compound exhibiting the diffraction pattern of FIG. 1B in powder X-ray diffraction with Cu—Kα ray, and thermal analysis diagram (TG-DTA) of FIG. 2B.

In the powder X-ray diffraction with Cu—Kα ray under the conditions shown later in Reference Example 1, the intensity and relative intensity of the diffracted ray depend on the particle size, shape, and crystallinity of the crystal of the hemihydrate, but the diffraction angle (plane spacing) does not vary.

Table 1 below shows the characteristic values of the typical diffraction peaks of the hemihydrate.

TABLE 1

Characteristic Values of Powder X-Ray Diffraction of Sodium Styrenesulfonate Hemihydrate with Cu—Kα Ray

| Diffraction angle (2θ) | d (Å) | Relative intensity ($I/I_0$) |
|---|---|---|
| 4.8 | 18.4 | 100% |
| 18.0 | 4.9 | 15 |
| 20.9 | 4.2 | 6 |
| 24.3 | 3.7 | 6 |

The crystal obtained under the conditions shown in Reference Example 1 shows a large endothermic peak at 70–80° C. in differential thermal analysis (DTA). The weight (TG) of the crystalline sample decreases in correspondence with the endothermic peak in an amount of 0.5 mol per mole of the sodium styrenesulfonate. The hemihydrate is a crystalline compound, and the particle size and shape of the crystal depend on the production conditions. The properties of the particle size and the like are not specially limited in the present invention. The sodium styrenesulfonate hemihydrate (hereinafter referred to simply as a "hemihydrate") exhibiting the analysis pattern and diagram of FIG. 1B and FIG. 2B has not been known until it has been found by the inventors of the present invention.

This hemihydrate is stable in chemical properties and crystal structure, and will neither polymerize nor lump during storage, transportation, and other handling.

The sodium styrenesulfonate has a double bond in the molecule, and is liable inherently to deteriorate chemically, to polymerize spontaneously, and to be oxidized, in a usual atmosphere. Nevertheless, the hemihydrate of the sodium styrenesulfonate is stable chemically, and is durable in long-term storage.

The crystal structure of the hemihydrate is stable, so that the hemihydrate is less liable to transform into another crystal structure such as sodium styrenesulfonate anhydrous and does not cause problems like lumping during long-term storage.

On the other hand, the crystal of the known conventional sodium styrenesulfonate is anhydrous. FIG. 1A and FIG. 2A respectively show a powder X-ray diffraction pattern and a thermal analysis diagram of the sodium styrenesulfonate anhydrous. These pattern and diagram are completely different from those shown in FIG. 1B and FIG. 2B characteristic to the hemihydrate. Therefore, the substances are obviously different from each other. In FIG. 2A, neither an endothermic peak nor decrease of the weight of crystallization water is observed, and only a small change caused by adsorbed water is observed at the low temperature range. This sodium styrenesulfonate anhydrous (hereinafter referred simply to as an "anhydrous") is poor in chemical stability and in crystal structure stability as mentioned above, and is liable to polymerize and lump during storage, transportation, and other handling.

The present invention relates also to a sodium styrenesulfonate composition which contains the hemihydrate at a content of not lower than 50% by weight. At the hemihydrate content of not lower than 50% by weight, the composition is stable chemically and crystallographically, and has a high commercial value without causing polymerization or lumping. The hemihydrate content of 70% by weight or higher is preferred, and the content of 90% by weight or higher is preferred more for the above effectiveness. In such a composition, the characteristics of the hemihydrate affect the coexisting anhydrous to improve the properties of the composition.

On the other hand, at the content of the anhydrous of not higher than 35% by weight, the composition can be stable also with the characteristics of the hemihydrate of less polymerization, less lumping, and high chemical and crystallographical stability. For more improvement, the anhydrous content is preferably not higher than 20% by weight, more preferably not higher than 10% by weight.

The water content in the composition is preferably in the range from 1% to 15% by weight for retardation of polymerization and lumping for higher commercial value thereof. The water content ranges more preferably from 2% to 10% by weight, still more preferably from 3% to 7% by weight for higher effects. The water content herein means the total amount of the water of crystallization of the hemihydrate and the adhering water. At a higher content of the hemihydrate, the amount of the water of crystallization is larger, which improves the handling properties of the composition.

The composition preferably contains sodium hydroxide at a content of 0.1% to 1.0% by weight for retardation of polymerization and lumping of the composition. The sodium hydroxide has effects of increasing the chemical and crystallographic stability characteristic of the hemihydrate, and further improves the stability of the coexisting anhydrous. The content of the sodium hydroxide ranges more preferably from 0.2% to 0.7% by weight, still more preferably from 0.2% to 0.4% by weight.

The composition of the present invention is preferably powdery. The shape of the powder particles is not limited, and may be in a flake, a prism, or an irregular shape. The composition in a powdery state has improved solubleness, and improved handling properties in weighing, although the powder is bulky. The particle diameter of the powder particles is usually not less than several microns and not more than several millimeters.

In the case where the composition of the present invention contains both the hemihydrate and the anhydrous mixedly, the hemihydrate particles and the anhydrous particles may be separately formed; or the particles may be constituted of the anhydrous in the interior portion and the hemihydrate in the exterior portion, or may be constituted of the hemihydrate in the interior portion and the anhydrous in the exterior portion. Preferably, the exterior of the particle is constituted of the hemihydrate for higher chemical and crystallographical stability of the composition.

The composition of the present invention usually contains sodium chloride, sodium bromide, sodium iodide, sodium sulfate, or the like as minor components in addition to the main components including the hemihydrate, the anhydrous, moisture, and sodium hydroxide. The minor components are formed in the sodium styrenesulfonate production process, but affect little the stability of the composition. However, a higher content of the minor components lowers the content of the sodium styrenesulfonate, and may cause a problem in use thereof. Therefore, the minor component content is preferably lower, and is not higher than 5% by weight, more preferably not higher than 3% by weight.

The composition of the present invention contains additionally a polymerization inhibitor. The polymerization inhibitor usually includes nitrite salts, hydroquinone, and hydroquinone monomethyl ether, and retards the spontaneous polymerization of the sodium styrenesulfonate during storage and transportation. Conventional sodium styrenesulfonate anhydrous compositions contain the inhibitor at a content of as high as several thousand ppm by weight. In the composition of the present invention, the inhibitor content may be reduced to 100 ppm by weight or lower, or further reduced to 10 ppm by weight or lower since the stability of the sodium styrenesulfonate is extraordinary high.

The processes for producing the sodium styrenesulfonate hemihydrate, and the composition thereof are described below in detail. However, the processes are not limited thereto.

In one production process of the present invention, the sodium styrenesulfonate is produced in the present invention by reaction of an aqueous β-haloethylbenzenesulfonic acid solution with an aqueous sodium hydroxide solution at a temperature of 60° C. or higher.

The halogen of the β-haloethylbenzenesulfonic acid and/or the sodium salt thereof includes chlorine, bromine, and iodine. Of the halogens, bromine is preferred in view of the cost and the reactivity. The concentration of the β-haloethylbenzenesulfonic acid in the aqueous solution of the β-haloethylbenzenesulfonic acid and/or the sodium salt thereof is not lower than 50% by weight, preferably not lower than 60% by weight, still more preferably not lower than 70% by weight. The aqueous solution of the β-haloethylbenzenesulfonic acid and/or the sodium salt thereof may contain, as the impurity, sulfuric acid, hydrogen halide acids such as hydrogen chloride, hydrogen bromide, and hydrogen iodide, salts thereof, and the like.

The sodium hydroxide is used in an amount necessary for forming sodium styrenesulfonate: specifically, 2–4 moles, preferably 2–3 moles of sodium hydroxide per mole of β-haloethylbenzenesulfonic acid, and 1–2 moles, preferably 1–1.5 moles of sodium hydroxide per mole of sodium β-haloethylbenzenesulfonate. The sodium hydroxide may be a commercial product of a concentration of 48% by weight or may be a solution thereof diluted with water.

The solvent used generally is water, and thereto a polymerization inhibitor such as a nitrite salt is preferably added to inhibit the polymerization of the formed sodium styrenesulfonate.

The reaction is conducted at a temperature of 60° C. or higher to increase the reaction rate and to accelerate crystal growth of the formed sodium styrenesulfonate. The temperature is preferably 80° C. or higher, more preferably 90° C. or higher. At a lower reaction temperature, the vinyl group formation rate is lower, and the formed product has lower crystallinity, whereas at a reaction temperature higher than 110° C., the sodium styrenesulfonate may partially polymerize spontaneously.

In mixing the aqueous solution of β-haloethylbenzenesulfonic acid and/or sodium salt thereof with the aqueous solution of the sodium hydroxide, the former may be added into the latter; the latter may be added into the former; or the both solution may be added concurrently. However, the addition of the aqueous sodium hydroxide solution to the aqueous β-haloethylbenzenesulfonic acid solution may cause polymerization of the formed sodium styrenesulfonate.

The atmosphere for the reaction may be air, but nitrogen atmosphere is preferred for retarding the polymerization of the formed sodium styrenesulfonate.

In such a manner, the crystalline anhydrous is obtained. The crystal is substantially anhydrous, containing occasionally some hemihydrate depending on the reaction conditions. The anhydrous in a slurry changes little its crystal structure even when it is cooled to a temperature of 20–30° C.

The crystalline matter, as formed or after cooling, is separated by solid-liquid separation by centrifugation or a like method to obtain a wet cake. This wet cake is fluidized forcedly. This forced fluidization is the essential point of this invention.

The forced fluidization herein signifies physical or mechanical fluidization of the wet cake. The apparatus for the fluidization includes stirring blades, rotation drums, screw-blenders, single or double screw extruders, V-type blenders, fluidizing blenders, and so forth. For example, when the wet cake is blended by means of a single screw blender, the cake increases its free fluidity unexpectedly to come to have dry powder appearance. During the fluidization, the hemihydrate content increases gradually and the anhydrous content decreases correspondingly according to observation by X-ray diffraction (XRD). In other word, the anhydrous is transformed into the hemihydrate. The conditions of the forced fluidization such as temperature, time, and intensity are not specially limited, provided that the obtained sodium styrenesulfonate composition contains the hemihydrate at a content of 50% by weight or higher. Further, the content of the anhydrous in the composition is preferably not higher than 35% by weight.

At a relatively high fluidization temperature of 40° C. to 60° C., the anhydrous is transformed at a high rate into the hemihydrate, so that the fluidization treatment is completed in a short time. At a still higher temperature, the anhydrous is stable, and the transformation rate is lower, whereas, at a lower fluidization temperature of 10–40° C., the transformation rate is low, and the transformation takes long time. Therefore, the temperature is preferably in the range of 40° C. to 60° C.

The transformation rate depends also on the cake composition. At a higher concentration of sodium hydroxide, sodium bromide, or the like salt, the transformation proceeds at a lower rate. At a lower concentration of the salt, and at a higher content of water, the transformation proceeds at a higher rate. The water content is preferably not less than 3% by weight. The content of water in the cake is usually not lower than 3% by weight, causing no problem. When increase of the transformation rate is desired, or when the cake becomes dried to contain water at a lower content and the cake is mainly constituted of the anhydrous, spraying of water is effective in the forced fluidization.

The time for the forced fluidization is usually in the range of 0.2 to 5 hours. During the fluidization, the crystals are partly crushed. However, the crushing affects little the chemical and crystallographic stability of the hemihydrate to give the desired product. The transformation from the anhydrous into the hemihydrate proceeds in the respective particles from the exterior to the interior, retarding the polymerization and the lumping significantly. The forced fluidization for less than 0.2 hour is not sufficient since the transformation from the anhydrous to the hemihydrate does not proceed sufficiently in such a short time without giving the expected results, whereas the forced fluidization for longer than 5 hours is not necessary since the treated matter is substantially a hemihydrate and no additional effect can be achieved. Rather, a longer time of the fluidization causes crushing of the crystals to make the crystal particles fine.

The greater the intensity of the forced fluidization, the higher is the speed of the transformation from the anhydrous to the hemihydrate and the shorter is the time for obtaining the particles exhibiting the desired effect. However, excessively higher intensity of the forced fluidization will cause crushing of the crystal particles to form fine crystals, whereas a lower intensity thereof will reduce the transformation rate to require a longer time for achieving the desired effect.

In another process for production of sodium styrenesulfonate of the present invention, an aqueous solution of β-haloethylbenzenesulfonic acid and/or a salt thereof is reacted with an aqueous sodium hydroxide solution, the product is crystallized and separated by solid-liquid separation, and the obtained wet cake of the sodium styrenesulfonate anhydrous is exposed to an atmosphere at a temperature of not higher than 60° C. at a relative humidity of not lower than 50%.

During the exposure to the aforementioned atmosphere, the anhydrous content of the cake decreases with lapse of time, and the hemihydrate content increases correspondingly. In other words, the anhydrous is transformed into the hemihydrate by this exposure treatment. The contents of the hemihydrate and the anhydrous can be measured by X-ray diffraction (XRD). Thus, the chemically and crystallographically stable hemihydrate and the composition thereof are obtained. The atmosphere is preferably at a temperature ranging from 30° C. to 60° C., and at a relative humidity ranging from 50% to 90% to obtain the stable hemihydrate in a short time with ease of handling.

The other conditions such as the particle size and shape of the crystals of the cake are not specially limited, provided that the resulting composition contains sodium styrenesulfonate at a content of not lower than 50% by weight. Further, the content of the anhydrous is preferably not higher than 35% by weight.

For increasing effectively the rate of transformation into the hemihydrate, the wet cake is exposed to the aforementioned atmosphere with simultaneous forced fluidization. An example of the apparatus therefor is a ribbon blender equipped with a temperature sensor and a humidity sensor.

In a still another method for production of sodium styrenesulfonate of the present invention, an aqueous solution of β-haloethylbenzenesulfonic acid and/or a salt thereof is reacted with an aqueous sodium hydroxide solution, the product is crystallized, the sodium hydroxide concentration in the resulting sodium styrenesulfonate anhydrous slurry is adjusted to be in the range of 0.1% to 3.0%, and the product is separated by solid-liquid separator such as a centrifuge.

At the sodium hydroxide concentration in the slurry adjusted to be within the range of 0.1% to 3% by weight, the anhydrous in the slurry is transformed into the hemihydrate. The adjustment, during the reaction and crystallization, of the sodium hydroxide concentration to 0.1–3% by weight is not effective for the transformation, giving substantially anhydrous, not hemihydrate. The concentration of the sodium hydroxide is preferably in the range of 0.5% to 2% by weight to obtain a composition containing the hemihydrate at a high content and sodium hydroxide at an appropriate content. In this concentration range, the hemihydrate composition having high stability can be produced.

The adjustment of the sodium hydroxide concentration can be conducted by neutralization with hydrogen halide acid such as hydrochloric acid and hydrobromic acid, sulfuric acid, or a like acid, dilution with water, or a like method.

The other conditions such as the treatment time, the stirring, and the salt concentration in the mother liquor are not specially limited, provided that the resulting composition contains sodium styrenesulfonate at a content of not lower than 50% by weight. Preferably, the content of the anhydrous is not higher than 35% by weight.

The contents of the hemihydrate and the anhydrous can be measured by X-ray diffraction (XRD). By the above process, the chemically and crystallographically stable hemihydrate, and the composition thereof can be obtained.

In a further method for production of sodium styrenesulfonate of the present invention, an aqueous solution of β-haloethylbenzenesulfonic acid and/or a salt thereof is reacted with an aqueous sodium hydroxide solution, the product is crystallized and separated by solid-liquid separation, and the obtained wet cake of the sodium styrenesulfonate anhydrous is washed with an aqueous sodium hydroxide solution of a concentration of not higher than 5% by weight.

The washing of the anhydrous with an aqueous sodium hydroxide solution of a concentration of 5% by weight or lower allows the anhydrous to transform into a hemihydrate. At the lower sodium hydroxide concentration in the washing solution, the rate of transformation to the hemihydrate is higher. With the decrease of the sodium hydroxide concentration, the transformation rate increases and reaches a constant rate at the sodium hydroxide concentration of about 1% by weight. The sodium hydroxide concentration is preferably in the range of 1% to 3% by weight to obtain a composition containing the hemihydrate at a preferred content.

To the aqueous sodium hydroxide solution, a small amount of a nitrite salt is preferably incorporated to raise the stability of the composition.

The washing is preferably conducted successively after centrifugal solid-liquid separation of the solid anhydrous from the slurry. By such a washing operation, the washing time can be shortened, and dissolution of the crystal in washing is retarded. The solid-liquid separation and the washing may be conducted by the same centrifuge.

The other washing conditions such as the temperature of the washing liquid, the amount of the washing liquid, and the washing time are not specially limited, provided that the resulting composition contains sodium styrenesulfonate at a content of not lower than 50% by weight. Preferably, the content of the anhydrous is not higher than 35% by weight.

Examples and comparative examples of the present invention are shown below without limiting the invention.

Hereinafter, the unit "part" and "%" are based on weight.

REFERENCE EXAMPLE 1

In a stainless reactor having a jacket and equipped with a stirrer, were placed 1054 parts of aqueous 35% sodium hydroxide solution, and 1.2 parts of sodium nitrite. The solution was heated with stirring to 70° C. Thereto, 1012 parts of aqueous 70% β-bromoethylbenzene-sulfonic acid solution was added dropwise with stirring in three hours in nitrogen atmosphere. During the addition, the temperature of the reaction mixture rose owing to the reaction heat. The temperature was maintained at 90° C. The resulting slurry was cooled, and the crystalline sodium styrenesulfonate (A) was collected from the slurry by centrifugation to obtain a wet cake of the sodium styrenesulfonate.

The wet cake of the compound (A) was forcedly fluidized by a single screw blender at room temperature for 30 minutes to obtain a wet cake of compound (B).

The compounds (A) and (B) were examined by chemical analysis, and powder X-ray diffraction by Cu—Kα ray and thermal analysis under the conditions shown below. The compounds (A) and (B) contained sodium styrenesulfonate respectively at a content of 83.0%, and 83.5% by chemical analysis. FIGS. 1A and 1B show the powder X-ray diffraction patterns by Cu—Kα ray. FIGS. 2A and 2B show the thermal analysis diagrams. From FIGS. 1A and 1B, obviously the compound (B) had a crystal structure completely different from that of the compound (A). From FIGS. 2A and 2B, the compound (A) and the compound (B) were respectively an anhydrous, and a hemihydrate of sodium styrenesulfonate.

Apparatus and Conditions of Powder X-Ray Diffraction

Apparatus: Rigaku-Geigerflex RAD-1C (Rigaku Denki K.K.)
    X-ray: Cu—Kα
    Intensity: 40 KV, 30 mA
    Scanning speed: 2 deg./min.
    Chart speed: 20 mm/min.

Apparatus and Conditions of Thermal Analysis

Apparatus: TAS100 (Rigaku Denki K.K.)
    TG weight change: 5 mg,
    DTA: 100 µV,
    Amount of sample: 51 mg
    Atmosphere: Nitrogen, 45 mL/min.
    Temperature elevation: from room temperature to 200° C., 10° C./min.

EXAMPLE 1 AND COMPARATIVE EXAMPLE 1

One kilogram each of the wet cakes of the crystalline sodium styrenesulfonate (A) and (B) were separately enclosed and sealed tightly in a polyethylene bag, and stored at 25° C. After six-month storage, the crystalline matters were analyzed chemically to measure the change of the sodium styrenesulfonate content, and the occurrence of lumping of the crystals was examined.

Table 2 shows the results. The crystalline sodium styrenesulfonate anhydrous (A) solidified into a rigid mass during the six-month storage, and had to be crushed by a mortar before sample preparation for the chemical analysis, the powder X-ray diffraction, and the thermal analysis. The sodium styrenesulfonate in the crystalline anhydrous (A) polymerized at a polymerization degree of about 10% by the six-month storage according to the chemical analysis.

On the other hand, the crystalline sodium styrenesulfonate hemihydrate (B) did not solidify at all. The sodium styrenesulfonate content thereof did not change at all without polymerization by the six-month storage. The crystal structure of the hemihydrate was retained during the storage.

TABLE 2

|  | Example 1<br>Sodium styrene-<br>sulfonate<br>hemihydrate (A) | Comparative<br>Example 1<br>Sodium styrene-<br>sulfonate<br>anhydrous (B) |
| --- | --- | --- |
| Storage Period | 6 Months | 6 Months |
| Sodium styrene-<br>sulfonate content<br>(% by weight) | 83.0% → 83.2% | 83.5% → 75.2% |
| Polymerization | No | Polymerization<br>degree: 10% |
| Lumping | No | Solidified rigidly |

EXAMPLE 2

The wet cake of the sodium styrenesulfonate hemihydrate (B) prepared in Reference Example 1 was dried by hot air at 50° C. for 4 hours to obtain crystals of a high sodium styrenesulfonate content. After the drying, the powder X-ray diffraction pattern by Cu—Kα ray thereof was the same as that of FIG. 1B, whereby the crystals were confirmed to retain the hemihydrate structure.

By the drying treatment, the sodium styrenesulfonate content in the crystalline matter (B) increased from 83.5% to 88.9%, and the salt did not polymerize all.

The dried salt was sealed and stored in a polyethylene bag in the same manner as in Example 1 and Comparative Example 1. After six-month storage, the hemihydrate structure was confirmed to be retained by the powder X-ray diffraction pattern, and was stored stably without lumping or polymerization.

COMPARATIVE EXAMPLE 2

The wet cakes of the anhydrous (A) and the hemihydrate (B) of the sodium styrenesulfonate prepared in Reference Example 1 were separately dried by hot air at 90° C. for 6 hours to obtain crystals of a high sodium styrenesulfonate content. After the drying, the powder X-ray diffraction patterns by Cu—Kα ray thereof were the same as that of FIG. 1A, whereby the dried crystalline salts were confirmed both to be the anhydrous.

By the drying treatment, the sodium styrenesulfonate content of the crystalline matter (A) increased from 83.0% to 89.3%, and that of the crystalline matter (B) increased from 83.5% to 90.2%, and polymerization was found to occur in the both crystalline matters at a polymerization degree of about 2% by the above heating at 90° C. for 6 hours.

In separate experiments, to prevent the decomposition and the polymerization, a large amount of sodium nitrite was added before the start of the reaction for formation of the salts (A) and (B), but the effect was not significant.

The aforementioned dried crystalline salts (A) and (B) in this Example were sealed and stored separately in a polyethylene bag in the same manner as in Example 1 and Comparative Example 1. After six-month storage, both of the crystalline salts caused partial lumping, and the sodium styrenesulfonate contents decreased by about 10% by polymerization and decomposition thereof.

EXAMPLE 3

The wet cakes of the anhydrous (A) and the hemihydrate (B) of sodium styrenesulfonate obtained in Reference Example 1 were exposed to the atmosphere of a relative humidity of 50% at a temperature of 60° C. for 10 hours by means of the apparatus (thermo-hygrostat) shown below. The both cakes showed the powder X-ray diffraction patterns by Cu—Kα ray and the thermal analysis diagrams which are nearly the same as the ones in FIG. 1B and FIG. 2B, respectively, whereby the cakes were confirmed to be sodium styrenesulfonate hemihydrate with a small amount of the anhydrous remaining.

Thermo-Hygrostat Apparatus
Apparatus: ADVANTEC AGX-325
CONSTANT TEMP HUMIDITY INCUBATOR

EXAMPLE 4

Sodium styrenesulfonate anhydrous was prepared by reaction of an aqueous β-haloethylbenzenesulfonic acid solution with an aqueous sodium hydroxide solution and crystallized in the same manner as in Reference Example 1. To the slurry, 413 parts of water was added with stirring to adjust the sodium hydroxide concentration in the liquid to 1%, and the slurry was kept in that state with stirring for one hour.

The cake separated from the slurry by centrifugation showed the powder X-ray diffraction pattern by Cu—Kα ray and the thermal analysis diagram which are nearly the same as the ones in FIG. 1B and FIG. 2B, respectively, whereby the cake was confirmed to be a composition mainly composed of sodium styrenesulfonate hemihydrate with a small amount of the anhydrous remaining.

EXAMPLE 5

A slurry of crystalline sodium styrenesulfonate anhydrous was prepared by reaction of an aqueous β-haloethylbenzenesulfonic acid solution with an aqueous sodium hydroxide solution and crystallized in the same manner as in Reference Example 1. The slurry was subjected to centrifugation to separate the solid. The obtained wet cake was rinsed with an aqueous 5 wt % sodium hydroxide solution containing a small amount of sodium nitrite. The rinsed cake showed the powder X-ray diffraction pattern by Cu—Kα ray and the thermal analysis diagram which are nearly the same as the ones in FIG. 1B and FIG. 2B, respectively, whereby the cake was confirmed to be a composition mainly composed of sodium styrenesulfonate hemihydrate with a small amount of the anhydrous remaining.

The present invention relates to a novel sodium styrenesulfonate hemihydrate, a composition thereof, and a process for production thereof as described above. The present invention solves entirely the chemical and physical problems of high polymerization tendency, low stability, lumping during storage, and so forth involved in the conventional sodium styrenesulfonate anhydrous. Therefore, the present invention is highly useful industrially. The process of the present invention provides stably the hemihydrate, and the composition thereof economically with high operability without a special apparatus or a special chemicals.

What is claimed is:

1. Sodium styrenesulfonate hemihydrate, produced by transformation of sodium styrenesulfonate anhydrous.

2. A sodium styrenesulfonate composition, containing the hemihydrate of sodium styrenesulfonate at a content of not lower than 50% by weight.

3. The sodium styrenesulfonate composition according to claim 2, containing sodium styrenesulfonate anhydrous at a content of not higher than 35% by weight, and water at a content of from 1% to 15% by weight.

4. The sodium styrenesulfonate composition according to claim 2, containing sodium hydroxide at a content of from 0.1% to 1.0% by weight.

5. The sodium styrenesulfonate composition according to claim 2, wherein the composition is in a form of a powder.

6. A process for producing the sodium styrenesulfonate hemihydrate set forth in claim 1, comprising reacting an aqueous solution of β-haloethylbenzenesulfonic acid and/or a sodium salt thereof with an aqueous solution of sodium hydroxide at a temperature of not lower than 60° C. to deposit sodium styrenesulfonate anhydrous, collecting the deposit by solid-liquid separation in a state of a wet cake, and fluidizing forcedly the wet cake.

7. A process for producing the sodium styrenesulfonate composition set forth in claim 2, comprising reacting an aqueous solution of β-haloethylbenzenesulfonic acid and/or a sodium salt thereof with an aqueous solution of sodium hydroxide at a temperature of not lower than 60° C. to deposit sodium styrenesulfonate anhydrous, collecting the deposit by solid-liquid separation in a state of a wet cake, and fluidizing forcedly the wet cake.

8. A process for producing the sodium styrenesulfonate hemihydrate set forth in claim 1, comprising reacting an aqueous solution of β-haloethylbenzenesulfonic acid and/or a sodium salt thereof with an aqueous solution of sodium hydroxide at a temperature of not lower than 60° C. to deposit sodium styrenesulfonate anhydrous, collecting the deposit by solid-liquid separation in a state of a wet cake, and exposing the wet cake to an atmosphere at a temperature of not higher than 60° C. at a relative humidity of not lower than 50%.

9. A process for producing the sodium styrenesulfonate composition set forth in claim 2, comprising reacting an aqueous solution of β-haloethylbenzenesulfonic acid and/or a sodium salt thereof with an aqueous solution of sodium hydroxide at a temperature of not lower than 60° C. to deposit sodium styrenesulfonate anhydrous, collecting the deposit by solid-liquid separation in a state of a wet cake, and exposing the wet cake to an atmosphere at a temperature of not higher than 60° C. at a relative humidity of not lower than 50%.

10. A process for producing the sodium styrenesulfonate hemihydrate set forth in claim 1, comprising reacting an aqueous solution of β-haloethylbenzenesulfonic acid and/or a sodium salt thereof with an aqueous solution of sodium hydroxide at a temperature of not lower than 60° C. to deposit sodium styrenesulfonate anhydrous, and adjusting the concentration of the sodium hydroxide in the reaction mixture to be in the range of 0.1% to 3% by weight.

11. A process for producing the sodium styrenesulfonate composition set forth in claim 2, comprising reacting an aqueous solution of β-haloethylbenzenesulfonic acid and/or a sodium salt thereof with an aqueous solution of sodium hydroxide at a temperature of not lower than 60° C. to deposit sodium styrenesulfonate anhydrous, and adjusting the concentration of the sodium hydroxide in the reaction mixture to be in the range of 0.1% to 3% by weight.

12. A process for producing the sodium styrenesulfonate hemihydrate set forth in claim 1, comprising reacting an aqueous solution of β-haloethylbenzenesulfonic acid and/or a sodium salt thereof with an aqueous solution of sodium hydroxide at a temperature of not lower than 60° C. to deposit sodium styrenesulfonate anhydrous, collecting the deposit by solid-liquid separation in a state of a wet cake, and washing the wet cake with an aqueous sodium hydroxide solution of a concentration of not higher than 5% by weight.

13. A process for producing the sodium styrenesulfonate composition set forth in claim 2, comprising reacting an aqueous solution of β-haloethylbenzenesulfonic acid and/or a sodium salt thereof with an aqueous solution of sodium hydroxide at a temperature of not lower than 60° C. to deposit sodium styrenesulfonate anhydrous, collecting the deposit by solid-liquid separation in a state of a wet cake, and washing the wet cake with an aqueous sodium hydroxide solution of a concentration of not higher than 5% by weight.

* * * * *